United States Patent
Carroll et al.

(10) Patent No.: US 6,471,693 B1
(45) Date of Patent: Oct. 29, 2002

(54) CATHETER AND SYSTEM FOR MONITORING TISSUE CONTACT

(75) Inventors: Sean Carroll, Beaconsfield; George Klein, London, both of (CA)

(73) Assignee: Cryocath Technologies Inc., Kirkland (CA)

(*) Notice: Subject to any disclaimer, the term of this patent is extended or adjusted under 35 U.S.C. 154(b) by 0 days.

(21) Appl. No.: 09/393,461

(22) Filed: Sep. 10, 1999

(51) Int. Cl.[7] .............................................. A61B 18/02
(52) U.S. Cl. ........................................... 606/21; 606/23
(58) Field of Search ..................................... 606/20–26

(56) References Cited

U.S. PATENT DOCUMENTS

| | | | |
|---|---|---|---|
| 5,643,255 A | 7/1997 | Organ | 606/41 |
| 5,667,505 A | 9/1997 | Štraus | 606/24 |
| 5,743,903 A | 4/1998 | Stern et al. | 606/31 |
| 5,759,182 A | 6/1998 | Varney et al. | 606/21 |
| 5,810,802 A | 9/1998 | Panescu et al. | 606/31 |
| 6,270,493 B1 * | 8/2001 | Lalonde et al. | 606/23 |

* cited by examiner

Primary Examiner—Lee Cohen
(74) Attorney, Agent, or Firm—Christopher & Weisberg, P.A.

(57) ABSTRACT

A cryocatheter for treatment of tissue has a tip adapted to provide a signal indicative of the quality and/or orientation of the tip contact with surrounding tissue. In one embodiment, a signal conductor extends through the catheter to the tip and connects to a thermally and electrically conductive shell or cap that applies an RF current to the region of tissue contacted by the tip. The tissue impedance path between the signal lead and a surface electrode mounted on the patient's skin is monitored to develop a quantitative measure of tissue contact at the distal tip, which is preferably displayed on the screen of a catheter monitoring console. In yet a further embodiment, the catheter is provided with a split tip having temperature monitoring sensors, such as thermistors, mounted on opposed halves of the tip so as to sense temperature on two sides of the catheter axis. The thermistor signals are processed to determine and display differential temperature between the two sides of the tip, thus revealing which side lies in contact. In yet a further aspect of the first embodiment, two separate and distinct high frequency electrical signals are applied to the two halves of a split metal shell or cap at the tip. Signals received at the surface electrode are filtered into first and second frequency components, and these are processed to determine the relative magnitude of the signal or the impedance of the path for each of the injected signals to determine and display the tissue contact orientation of the catheter. The catheter preferably has two separate cooling chambers within the cooling tip, positioned with one chamber on each side of the axis, and a separate cooling inlet to each chamber is switched on by a valve which directs the flow of coolant to the contact side during active cryotreatment. In another embodiment, the cap provides an RF electrode that may be opposed to the cooling side so that either the cryogenic or the RF ablation side may be rotated into contact to selectively heat or cool, or in representative protocol treat, then thaw, the same tissue site.

11 Claims, 3 Drawing Sheets

CATHETER AND SYSTEM FOR MONITORING TISSUE CONTACT

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present application relates to cryocatheters and wands, i.e. to catheters and wands which are used to treat tissue by cooling contact. Such implements, henceforth generically referred to herein as "cryocatheters" or simply "catheters" have an elongated body through which a cooling fluid circulates to a tip portion which is adapted to contact and cool tissue. In general, cryocatheters may be used to lower the temperature of tissue, such as cardiac wall tissue, to an extent such that signal generation or conduction ceases and allows one to map or confirm that the catheter is positioned at a particular lesion or arrhythmia conduction site. They may also be configured for ablation treatment, to cool the tissue to a much lower level at which freezing destroys the viability of the tissue, and, in the case of cardiac tissue, permanently removes it as a signal generating or signal conducting locus. Such devices are also useful for destruction of tissue at other body sites, such as the ablation of tumorous, diseased, precancerous or congenitally abnormal tissue in various vessel or organ systems.

Cryocatheters may be adapted for endovascular insertion, or for insertion along relatively confined pathways, for example through a body lumen, or through a small incision to and around intervening organs, to reach an intended ablation site. As such, they are characterized by an elongated body through which the cooling fluid must circulate, and a tip or distal end portion where the cooling is to be applied. The requirement that the coolant be localized in its activity poses constraints on a working device. For example when the catheter contact must chill tissue to below freezing, the coolant itself must attain a substantially lower temperature. Furthermore the rate of cooling is limited by the ability to supply coolant to and circulate it through the active contact region, and the efficacy of the contact region itself is further limited by geometry and physical properties that affect its ability to conduct heat into the tissue. The achievable rate of cooling may be impaired by warming due to residual circulation, and it also changes depending upon the effectiveness of thermal contact, e.g. upon the contact area and contact pressure between the catheter and the tissue, as well as being influenced by ice accumulations or other artifacts or changes due to the freezing process itself. Moreover, it is a matter of some concern that proximal, adjacent or unintended tissue sites should not be exposed to harmful cryogenic conditions. These somewhat conflicting requirements make the implementation of an effective cryocatheter a complex matter.

One approach has been to provide a phase change coolant which is pumped as a liquid to the tip of the catheter and undergoes its phase change in a small chamber located at the tip. The wall of the chamber contacts adjacent tissue directly to effect the cooling or ablation treatment. Such a device can treat or achieve a relatively high rate of heat energy transfer. Moreover, by employing a phase change refrigerant which may be injected at ambient temperature along the body of the catheter and undergo expansion at the tip, the cooling effect may be restricted to the localized treatment region surrounding the tip portion of the device. The dimensions of catheter construction, particularly for an endovascular catheter, require that the phase change coolant be released from a nozzle or tube opening at a relatively high pressure, into a relatively small distal chamber of the catheter. After the fluid expands in the distal chamber and cools the walls, it is returned through the body of the catheter to a coolant collection system, preferably in the form of a recirculation loop.

Catheters or treatment wands of this type for endovascular or endoscopic use generally have a relatively symmetrical profile such as a pencil-like cylindrical shape or a bullet-like shape, and they may include various steering mechanisms for curving the tip to urge it against the tissue which is to be treated. Fluoroscopic visualization may be used both for positioning the catheter tip initially and for observing the progress of ice formation. However, the cooling effect is extremely local, relying on thermal conduction through contact, and the method of visualization may involve a plane projection, or may otherwise lack precision or resolution. Also, because of the extreme temperatures involved, the tip of the catheter may freeze to tissue which it contacts, preventing any further adjustment or repositioning of the tip once cooling has started. Moreover, if the catheter construction involves any degree of asymmetry, the fluoroscopic representation may be insufficient to determine the effective area of contact or expected cooling profile in surrounding tissue.

It has been proposed, for example in U.S. Pat. 5,667,505, that because of the impossibility of measuring the tip-to-tissue contact, one instead measure the temperature of a heat exchanger, and utilize a standard heat capacity measurement to develop appropriate control signals. Furthermore, with these and other types of ablation catheters, various detection systems have been proposed for determining the degree of contact or the extent of heating. See, for example, U.S. Pat. Nos. 5,743,903, No. 5,810,802, No. 5,759,182 and No. 5,643,255. However, to the best of applicant's knowledge, such devices do not address the need for a simple positioning system for a cryogenic treatment catheter.

Accordingly, there remains a need for a cryocatheter tip construction that effectively determines, reports or controls tissue contact.

There is also a need for a cryocatheter construction that more effectively cools contacted tissue.

There is further a need for a cryocatheter positioning system which is controllable to apply cooling to a predetermined tissue region.

SUMMARY OF THE INVENTION

One or more of the foregoing desirable objects are achieved in accordance with embodiments of the present invention by a cryocatheter for treatment of tissue wherein the tip of the catheter is adapted to provide a signal indicative of the quality and/or orientation of the tip contact with surrounding tissue. In one embodiment, a signal conductor extends through the catheter to the tip and connects to a thermally and electrically conductive shell or cap to apply a high frequency electrical signal to the region of tissue contacted by the tip. A surface electrode is mounted on the patient's skin, and the tissue impedance path between the signal lead and the surface electrode is monitored to develop a quantitative measure of tissue contact in the cooling region of the distal tip. Preferably this measure is displayed on the screen of a catheter monitoring console. In yet a further embodiment, the outer portion of the tip is provided with a split thermally conductive jacket, and temperature monitoring sensors, such as thermistors or thermocouples, are mounted on both halves of the tip so as to sense temperature separately on two opposite sides of the catheter axis. The thermal signals are processed to indicate and display the differential temperature between the two sides of the tip, thus providing an indication of which side lies in contact with tissue.

In yet another aspect of the first embodiment utilizing a split conductive shell or cap, two separate and distinct high frequency electrical signals are applied to the two halves of the split tip. In that case, the signal received at the surface electrode is filtered into first and second frequency components, and these are processed to determine the relative strength of each signal component to provide an indication of the relative impedance of the path for each signal, and thus the console determines and displays the tissue contact orientation of the catheter tip itself. The system of this embodiment preferably utilizes a catheter which has separate cooling or refrigerant expansion or circulation chambers within the cooling tip. These may be positioned so that one chamber lies on each side of the axis at the tip region, and each is associated with its own thermistor or other sensor, and its own conductive wall portion. A controller monitors the temperature sensor or RF conduction of the signal electrode associated with each chamber, and the control console display indicates the tissue-contacting side of the catheter. This cryocatheter preferably includes a separate cooling inlet to each chamber, and a mechanism in or connected to the handle for directing the flow of coolant to one or the other chamber during active cryotreatment. The console may further include a controller to automatically control the valve to direct coolant to the tissue-contacting side.

BRIEF DESCRIPTION OF THE DRAWINGS

The invention will be more fully understood from the detailed discussion below of several examples taken in conjunction with drawings of illustrative embodiments, in which.

DETAILED DESCRIPTION OF THE DRAWINGS

Figure 1:
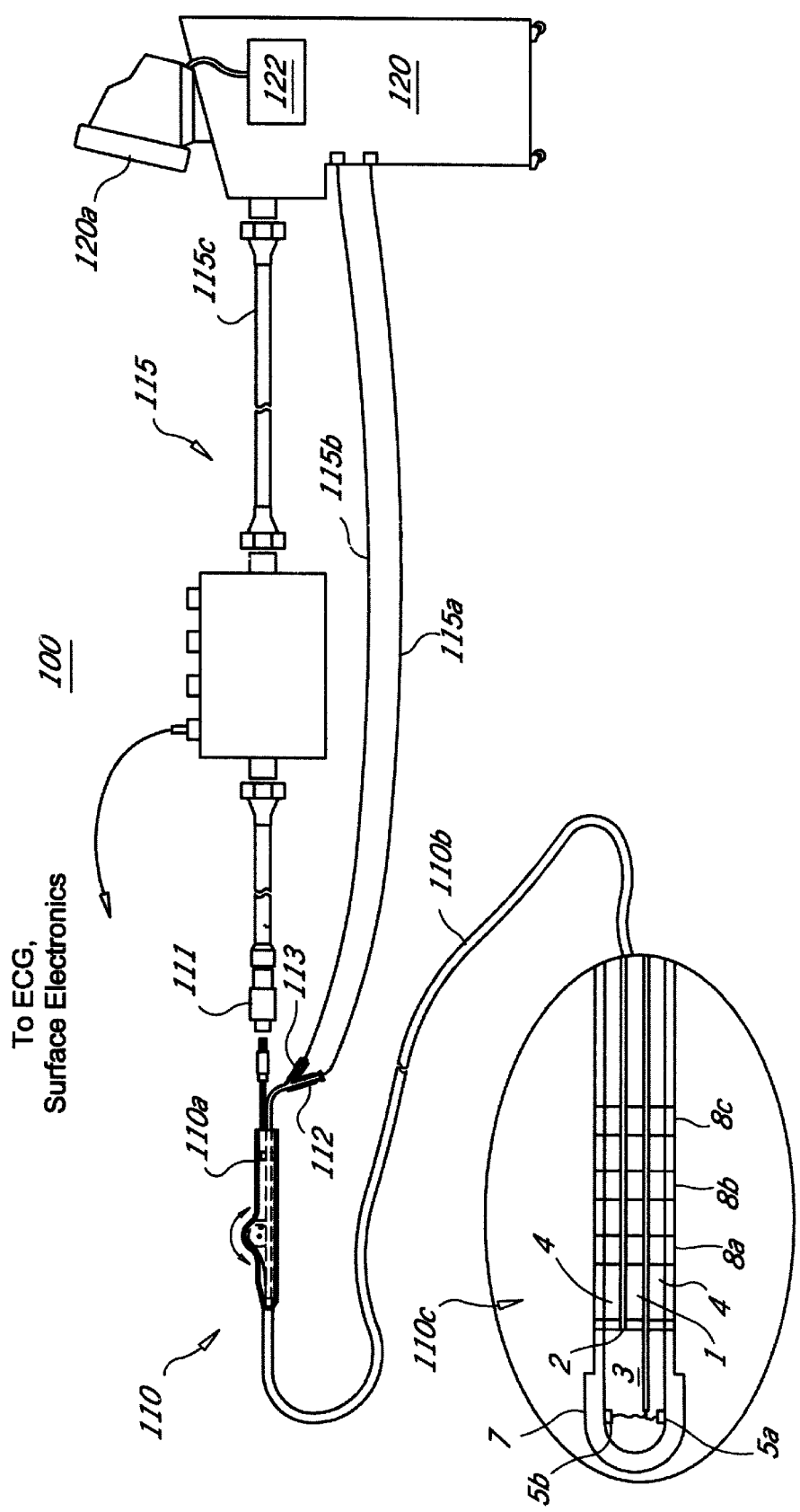
FIG. 1 shows a cryoablation catheter and system of the present invention.

FIG. 1 shows a cryogenic treatment system 100 illustrating representative elements thereof System 100 includes a treatment catheter 110 having a handle 110a, and elongated cryogen transporting body 110b and a catheter tip 110c. The catheter 110 is connected by various conduits or cables 115 to a console 120 which may, for example, perform control and monitoring functions, and may have a display monitor 120a and other data entry or display accessories such as a keyboard, a printer and the like. The lines 115 may include a coolant injection line 115a, a coolant return line 115b, and electrical cabling 115c which may carry outputs of various cardiac sensing, thermal sensing, mapping or other elements such as are commonly used for catheter treatment or monitoring. As shown, the handle 110a is equipped with input ports for an electrical connector 111, a coolant injection tube connector 112, and a return tube connector 113. These connect by various internal junctions or tubes passing through the handle and elongated body 110b to the distal tip of the catheter. The handle may also include deflection mechanisms, various control assemblies, e.g., switches or valves, as well as safety detection or shutdown elements (not illustrated), some of which are discussed further below.

Figure 2:
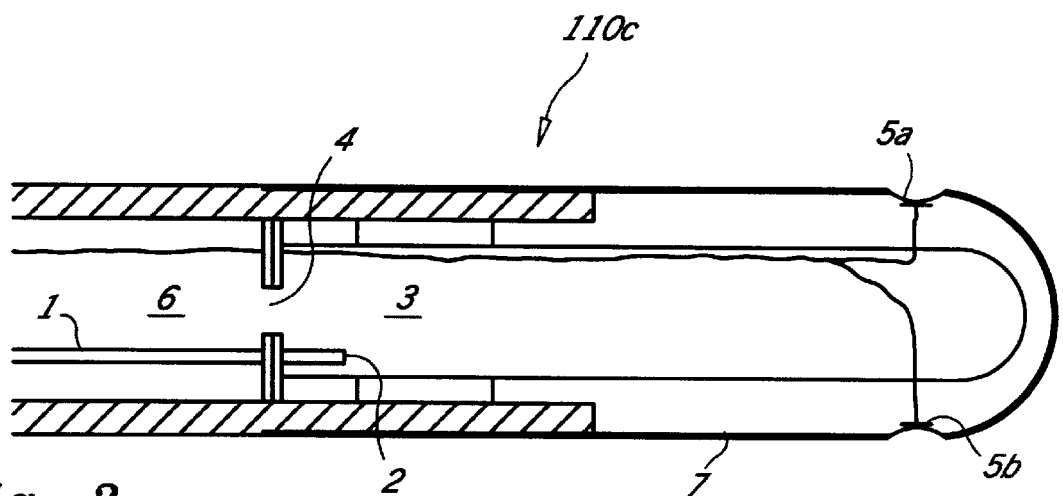
FIG. 2 illustrates a first embodiment of a catheter of the invention.

As shown schematically in FIG. 2, the coolant is carried to the tip through a tube 1 and enters a chamber 3 at the end of the catheter tip 110c via a nozzle 2 at the end of the tube to expand in a small contained region forming the active cooling region of the tip of the catheter. By way of example, the tube 1 may run centrally within the elongated body 110b, and the portion of the body lumen outside of tube 1 may form a return passage for spent coolant. After coolant exits from an orifice 2 at the end of the tube, it returns through the space 6 surrounding the tube 1 to the fluid return connector 113 of the handle (FIG. 1). The return passage for expended coolant may be a vacuum passage, thus assuring that leakage out of the catheter into the bloodstream does not occur, and providing some additional thermal insulation of the fluid line running along its interior.

In the illustrated embodiment, the chamber 3 in which coolant is released from the nozzle 2 and whence it returns to the return passage via opening 4, defines the cooling region of the catheter tip. This chamber may be short, less than a few centimeters long, and located at the very tip of the catheter or slightly proximal thereto. The active cooling chamber has a thermally conductive wall 7 for efficiently conducting heat from the adjacent tissue, and for the illustrated endovascular embodiment this takes the form of a metal cap that may advantageously be steered into contact with the tissue by a simple bending deflection of the tip region. In accordance with a principal aspect of the present invention, the chamber is also equipped with elements for sensing which portion of the tip has been brought into contact with tissue. In the illustrated embodiment, this is achieved using first and second thermocouples 5a, 5b positioned on opposite sides of the chamber 3. In the case of a cardiac catheter, one or more ring electrodes 8a, 8b, 8c (FIG. 1) may be positioned at the catheter tip for performing signal sensing and/or position monitoring functions.

While the foregoing description describes a cryogenic catheter system in general terms with several elements which are or may be useful in such a system, applicant specifically contemplates as a preferred embodiment a cryoablation system that utilizes a phase change coolant injected through the coolant line 1 to expand in the chamber 3 at the tip of the catheter, and return via a vacuum or suction passage to the return connection 113 at the catheter handle. In a system of this type developed by the assignee of the present invention, the phase change material is provided at ambient temperature but relatively high pressure through the handle and body 110a, 110b of the catheter, such that cooling only occurs upon release of pressure and expansion within the chamber 3 at the tip of the catheter. Operation of this device involves controlling the timing and amount of coolant injected through the inlet tube 1, and/or the injection pressure, which may, for example, be a pressure up to about 500 psig. The entire catheter with such a localized cooling mechanism may be dimensioned to fit in a No. 9 French introducer or smaller. Similar coolant systems may be incorporated in hand-held cryotreatment or ablation units for endoscopic application.

In accordance with the principal aspect of the present invention, the sensor signals, for example from the thermocouples 5a, 5b are provided to the monitor and control console 120 which may in addition receive other system inputs from sensors related to the cooling system, cardiac sensing electrodes or positioning or mapping elements of the catheter system. As shown, the controller 120 communicates with or includes a processor 122 and the display 120a, and it may operate in a manner known in the art to perform such display functions as for example overlaying a radiographic image of the catheter and patient with various synthetically created images, for example, representing mapping points or thermal or physiological data derived from sensor measurements. The controller 120 may also produce output signals, for example to control the flow of coolant in response to detected trigger signals, temperature states or other conditions in an automated program or manually controlled manner.

In an exemplary mode of operation for a system having opposed thermocouples 5a, 5b as shown in FIGS. 1 and 2, the processor 122 may simply detect the outputs of both thermistors and determine the difference in temperature between the two sensing positions. In that case, the colder sensor may correspond to the sensor on the side that directly contacts tissue (it being assumed, in the case of an endovascular or cardiac system, that blood flow has a warming effect on the cryocatheter).

Figure 3:
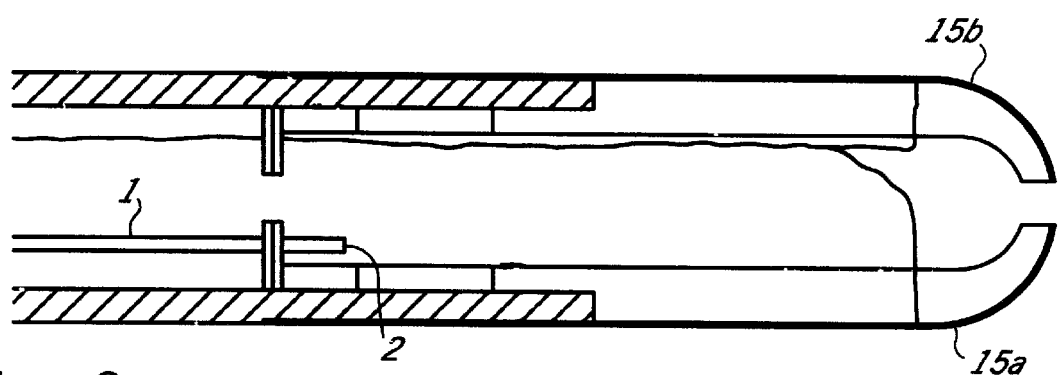
FIG. 3 illustrates a second embodiment of a catheter of the invention.

FIG. 3 shows another embodiment of a catheter system of the present invention. As shown in FIG. 3, the tip portion or tissue-contacting portion, when the chamber is located slightly proximal of the tip, is formed with a themally conductive outer shell or cap 15 which, as illustrated, is split into two halves 15a, 15b such that one half 15a covers one side of the catheter and another half 15b lies opposite, across the midplane or axis of the catheter. This split shell construction may be used with the catheter of FIGS. 1 and 2, in which case each of the thermocouples 5a, 5b is preferably mounted in contact with or in a slight recess at the surface of, a corresponding one of the half shells 15a, 15b. In that case the cap serves not only to enhance heat conduction through the chamber wall, but also to spread or uniformize the level of heat present generally at the side on which it is mounted. The thermally conductive halves 15a, 15b may extend for slightly different lengths along the axial direction of the catheter, making their positions and thus the catheter orientation visible radiographically, due to possible radiographic opacity of their structure and their distinct visual appearance on the display.

In accordance with another aspect of the invention, rather than employing thermal sensing elements 5a, 5b, the positioning system of the present invention may operate by means of impedance sensing to detect tissue contact or catheter orientation. In accordance with this aspect of the invention a body electrode is provided, such as a large area surface electrode, and the impedance path between each of the conductive shell pieces 15a, 15b and the body electrode is monitored. This may be done by applying a high frequency or alternating signal to the surface electrode and detecting the signal at a catheter lead extending from each of the separate shells 15a, 15b. This signal shall hereinafter be simply referred to as an "RF signal" although the term RF, as used in different technical fields and various countries is technically more restrictive than the intended class of alternating signal energy. The strength of the signal so detected provides an indication of impedance path between the respective catheter electrodes on the two sides of the cooling segment, and the surface electrode. Since the major portion of the tissue pathway is identical for both sides of the catheter, the detected impedance of the two halves will differ largely as a function of the local tissue contact at the cooling tip. Thus, it suffices to find the electrode having the lowest impedance, or to derive a measure, such as the ratio of the two signals, that may be used as a binary (GO/NO GO) indicator of which side is in contact. Thus, for example if the ratio of the signal strength at electrode 15a to that of electrode 15b is taken as the detection threshold, a ratio greater than one indicates that electrode 15a makes better electrical contact and a ratio less than one indicates that electrode 15b makes the better contact. As may be surmised from the discussion of the temperature differential, above, the foregoing rule would apply in circumstances where the catheter is used in a blood-free environment. When the catheter resides in a full vessel, then contact by the saline blood solution may provide a better electrical pathway. This results in the opposite detection algorithm, i.e., the low-impedance path is through the non-tissue-contacting side of the catheter.

As a variation on this detection method, the RF signals may be provided to the two separate shell portions 15a, 15b of the catheter of FIG. 3, and detected at the surface electrode. In this case, preferably signals of two different frequencies $f_1$, $f_2$ are provided at the catheter tip to the two electrically-separated electrode halves. The processor 122 of the controller 120 may then synchronously demodulate the detected signals arriving from the respective electrodes at the surface electrode, at their respective frequencies, cumulating and determining the strength of the signal over some time interval before taking a ratio of the detected signals. Again the relative impedance of the two pathways identifies which electrode has made contact with tissue.

Figure 4:
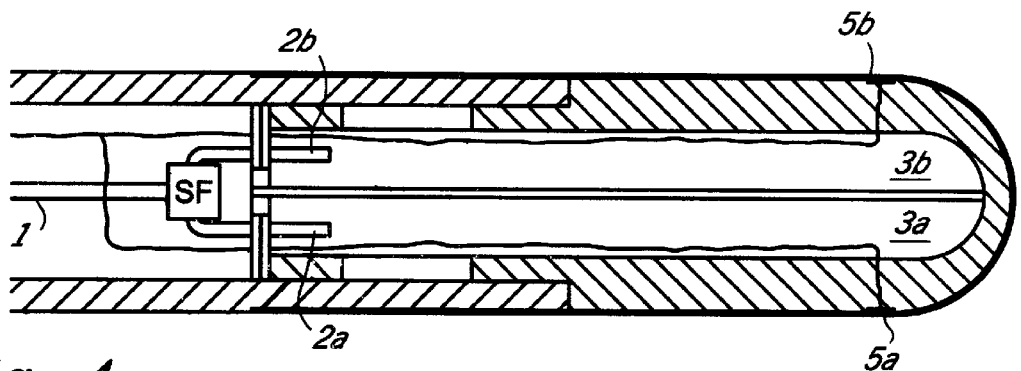
FIG. 4 shows a third embodiment of a catheter of the invention.
Figure 4A:
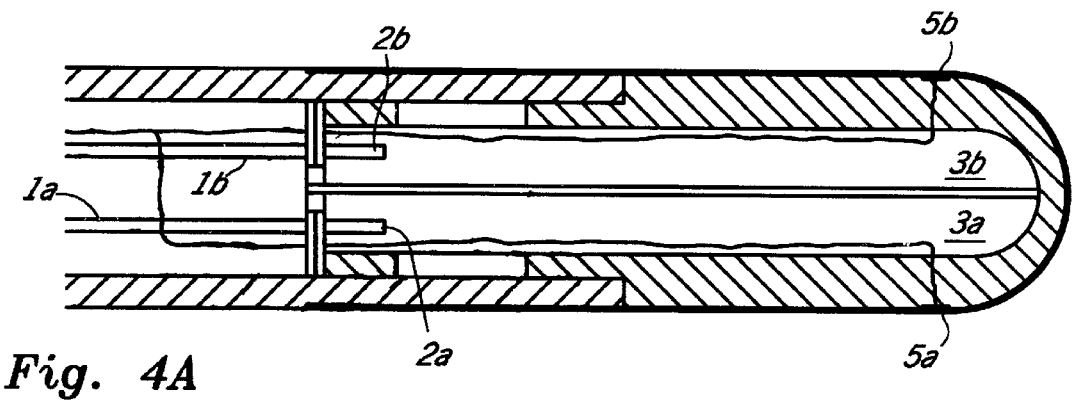
FIGS. 4A and 4B show further embodiments with alternative cooling arrangements.
Figure 4B:
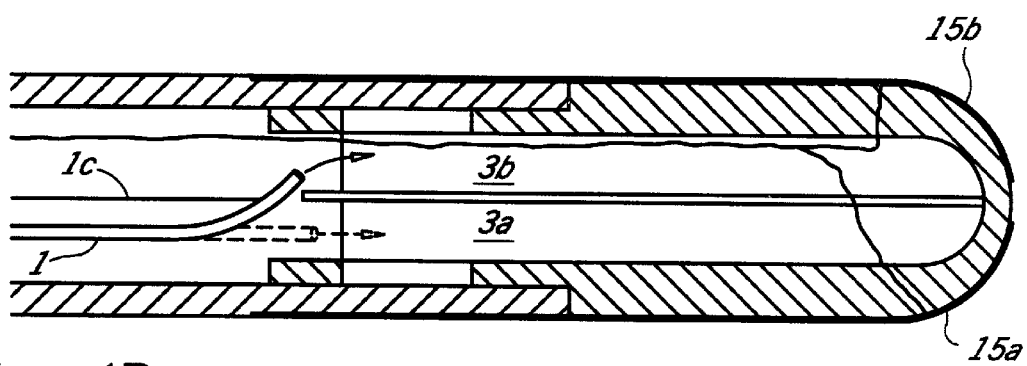

In accordance with a preferred aspect of the positioning system of the present invention, the cryocatheter has a cooling region comprised of two separate compartments 3a, 3b forming a split chamber as shown in FIG. 4. In this embodiment, coolant may be directed into either the first chamber 3a or a second chamber 3b lying on opposite sides of the catheter axis by corresponding fluid inlets 2a, 2b, respectively, attached to the fluid source. This may be done by providing a switched valve SF operably connecting either of the inlets. Alternatively, two separate supply lines 1a, 1b switched at the control console 120 or in the catheter handle may be employed, as indicated in FIG. 4A. Switched cooling may also be accomplished by providing a single coolant line 1 which is physically moved or steered by a steering wire 1c to direct its coolant into one or the other chamber as shown in FIG. 4B. Each of the chambers 3a, 3b is associated with one of the surface electrodes or conductive shell portions 15a 15b (FIG. 3), or thermal sensors (FIG. 2), and for example each of the half-jackets or electrodes 15a, 15b may form a wall of one of the chambers. When employed with temperature sensors such as thermistors, each chamber has a sensor mounted on its contact wall.

Operation of this split chamber or bifurcated embodiment proceeds as follows. The controller is configured to carry out a monitoring or an initial procedure wherein it detects the side of the catheter in contact with tissue. Then for cooling operation, the controller controls a valve which may for example be located in the handle of the catheter assembly so as to preferentially cool one of the chambers 3a or 3b which it has determined to reside in contact with the tissue. This allows the coolant to be more effectively used to cool the tissue side of the catheter. When the tissue contact detection mechanism is that of electrodes and RF signal impedance, the controller simply actuates a valve to direct coolant to the detected contacting side of the catheter. Preferably, the coolant may also be manually switched at the handle from one side to the other.

When the thermistor assembly as shown in FIG. 1 is employed as the contact detection mechanism, the controller preferably initiates a somewhat more complex initial procedure whereby each chamber 3a and 3b is cooled, simultaneously or successively, at a low level of cooling while the temperature response is measured. The processor then determines from the response which side is cooling more quickly or otherwise exhibits a thermal characteristic such that it is deemed to be in contact with body tissue. Based on this determination, the controller thereafter controls the cryogenic cooling regimen to preferentially cool that side of the catheter tip. Thus, the present invention contemplates a catheter wherein both the catheter cooling region and the catheter arrangement of sensors may discriminate between two sides, so as to detect the contacting side and then to more effectively cool the portion of the catheter that has contacted tissue.

The invention further contemplates that in embodiments wherein the tissue impedance is determined via signals conducted through a conductive cap or shell, this impedance may be detected by attaching the catheter to a conventional RF ablation catheter console, in which, for example, such impedance measurements are customarily performed to provide a control input for monitoring the degree of ablation and for the RF ablation power control. In that case, the catheter of the present invention may also operate as an RF ablation electrode with the metal cap 7, 15 driven by the RF catheter console. The conductive cap or shell may be split, and different regions of the cap may be connected to a bipolar RF driver so that ablation energy warms or ablates tissue at a gap between the bipolar electrodes. In this case, the electrode gap may be positioned so that the heating region is angularly offset around the catheter tip from the cooling wall of the cooling chamber. This allows the catheter to treat an identified site either by RF heating or by thermally conductive cooling, by simply rotating the catheter to position the cooling wall or the electrode gap at the intended site.

The invention being thus disclosed and several operative embodiments discussed, various additional constructions adapting the invention to known catheters and control systems, and other variations and modifications of the disclosed invention, will occur to those skilled in the art, and it will be understood that such adaptations, variations and modifications are all within the spirit and scope of the invention. Accordingly, the invention is not limited to the described embodiments, but encompasses all subject matter defined by or falling within the scope of the claims appended hereto and equivalents thereof.

What is claimed is:

1. A cryotreatment system, such system comprising
a cryotreatment unit including a handle, an elongated body and a cooling region, the cooling region having an outer shell and an interior through which cooling fluid passes to cool said outer shell contactable with body tissue, the outer shell further comprising
a first portion and
a second portion thermally and electrically independent of the first portion,
at least one contact monitor lead extending through said body to each of the first and second portions of the outer shell for developing a signal indicative of contact and
means responsive to said contact monitor lead for indicating tissue contact.

2. The cryotreatment system of claim 1, wherein said means for indicating tissue contact develops a differential signal indicating contact orientation of the cooling region.

3. The cryotreatment system of claim 1, wherein the means for indicating tissue contact determines contact from a temperature response characteristic.

4. The cryotreatment system of claim 1, wherein the means for indicating tissue contact determines contact from a temperature difference between the first half portion of the outer shell and the second half portion of the outer shell.

5. The cryotreatment system of claim 1, wherein the means for indicating tissue contact determines contact from relative conduction signal strength.

6. The cryotreatment system of claim 1, wherein the means for indicating tissue contact determines contact from the frequency of a conduction signal associated with cooling region contact orientation.

7. The cryotreatment system of claim 1, wherein said interior of said cooling region is divided into first and second subchambers, the cryotreatment unit further comprising a means for separately cooling each of the first and second subchambers.

8. The cryotreatment system of claim 1, wherein the cooling region is bounded by a split conductive shell, and further comprising an RF conductor extending through the elongated body to said shell for applying RF energy therethrough to surrounding tissue.

9. The cryotreatment system of claim 8, wherein said shell having a first portion substantially contiguous with said cooling region interior; and a second portion adjacent or opposed to said first portion, said RF conductor being connected to at least one of said first and second portions such that rotation of the cooling region positions the unit to apply RF energy to tissue at the cooling region.

10. A cryotreatment probe system, such system comprising
a cryotreatment probe including a handle, an elongated body and a treatment tip, the treatment tip containing a chamber through which cooling fluid circulates, the chamber having an outer wall contactable with body tissue, said wall having first and second distinct regions
at least one contact monitor lead extending through said body to the tip for indicating tissue contact and
a means responsive to said contact monitor lead for determining thermal contact orientation of the treatment tip,
wherein the chamber includes first and second selectively coolable compartments, and said means
i) determines which one of said first and second compartments thermally contacts tissue, and
ii) selectively cools said one compartment.

11. The cryotreatment probe system of claim 10, further comprising a controller and wherein the controller is operative to detect tissue contact and to selectively direct coolant to either of the first or second selectively coolable compartments.

* * * * *